United States Patent
Champaigne (10) Patent No.: US 8,091,406 B1
(45) Date of Patent: Jan. 10, 2012

(54) GAGE FOR MEASURING MINI-STRIP DISPLACEMENT FOR DETERMINING INTENSITY

(75) Inventor: Jack Champaigne, Mishawaka, IN (US)

(73) Assignee: Electronics Inc., Mishawaka, IN (US)

( * ) Notice: Subject to any disclaimer, the term of this patent is extended or adjusted under 35 U.S.C. 154(b) by 304 days.

(21) Appl. No.: 12/480,460

(22) Filed: Jun. 8, 2009

(51) Int. Cl.
*G01N 3/34* (2006.01)
(52) U.S. Cl. ............................................ 73/11.02
(58) Field of Classification Search .................. 73/11.02
See application file for complete search history.

(56) References Cited

U.S. PATENT DOCUMENTS

| | | | |
|---|---|---|---|
| 2,350,440 A | | 6/1944 | Almen |
| 5,297,418 A | | 3/1994 | Champaigne |
| 5,780,714 A | * | 7/1998 | Champaigne ............... 73/1.79 |
| 5,877,405 A | * | 3/1999 | Champaigne ............... 73/11.02 |
| 6,183,882 B1 | * | 2/2001 | Mannava et al. ............ 428/614 |
| 6,289,713 B1 | * | 9/2001 | Champaigne ............... 73/1.79 |
| 7,735,350 B2 | * | 6/2010 | Bailey et al. ............... 73/11.02 |

* cited by examiner

*Primary Examiner* — Lisa Caputo
*Assistant Examiner* — Octavia Davis
(74) *Attorney, Agent, or Firm* — Botkin & Hall, LLP (57) ABSTRACT

A gage for measuring deflection of a "mini-strip" used to determine peening intensity in small cavities and crevices of a work piece includes a pair of platforms made of a magnetic material spaced apart in a non-magnetic fixture a distance substantially the same as the length of the mini-strip. The platforms have a diameter slightly larger than the width of the mini-strip to provide support for both corners on each end of the mini-strip. A magnet for each of the platforms may be advanced toward and retracted from the platform to adjust the degree of magnetic attraction of the mini-strip. The platforms are stepped to define a shoulder and posts are offset from one of the platforms which cooperate to guide the user in proper placement of the strip. A plunger extended from the indicator engages the strip at substantially its midpoint, to thereby measure the deflection of the strip to give an indication of peening intensity.

14 Claims, 7 Drawing Sheets

GAGE FOR MEASURING MINI-STRIP DISPLACEMENT FOR DETERMINING INTENSITY

BACKGROUND OF THE INVENTION

This invention relates to the measurement of intensity in shot peening and shot blasting processes. Shot peening is a well established process for increasing the fatigue life and strength of metal products. In the shot peening process, the product undergoing peening is subjected to a stream of shot. The intensity of the peening process is a function of many factors, including the size and the velocity of the shot. Accordingly, it is necessary to regulate and confirm peening intensity, usually by the so-called Almen process, which uses Almen strips subjected to peening, and then measured by a gage as described in U.S. Pat. No. 2,350,440. In this process, a thin metal strip is placed on a fixture and peened for a predetermined time. Although the strip is initially flat, when subjected to the shot stream during peening, the strip will become curved. The amount of curvature is a function of peening intensity. Accordingly, by measuring the deflection of the test strip from its initial flat condition, an indication of peening intensity is determined.

Blast cleaning is a similar process in which an abrasive grit is blasted onto a surface to remove paint, etc. Since blast cleaning at high intensities may damage the surface, it is also necessary to determine the intensity. This is done similarly to the aforementioned process for measuring the intensity of shot peening.

Some products, which must be peened, have complex shapes such as narrow crevices or cavities. Oftentimes these cavities are points of increased stresses so that the area around these cavities will benefit from peening. The standard Almen strip, however, is too large to fit in many of these cavities, therefore, peening intensity cannot be easily confirmed. Oftentimes, the peening intensity in such cavities depends upon the peening media ricocheting off of the product or off of the walls of the peening chamber in which the peening takes place. Although the peening intensity inside of the cavity will be less than the intensity on the remainder of the product, the actual intensity is difficult to confirm.

The standard Almen strip is approximately three inches long and three quarters of an inch wide. Clearly, standard Almen strips are too large to fit into small crevices and cavities. Accordingly, so called "mini-strips" have been proposed in which the strips are one eighth of an inch wide and either one or two inches long. These mini-strips are small enough to fit into the cavities and crevices where a measurement of intensity is desired. These mini-strips however, are impossible to be measured using a standard Almen gage. The standard Almen gage uses contact balls to support the Almen strip but the mini-strips are too narrow to rest on all four contact balls. For this reason, a new gage providing stable measurements of the deflection of a mini-strip is required.

SUMMARY OF THE INVENTION

According to the invention, to measure arc height, the measurement used in determining intensity, the operator places a peened mini-test strip on a fixture having a flat and planar pair of support platforms on opposite ends of the strip. After peening, the test strip is defined by longitudinally and transversely curved surfaces. Accordingly, the four corners of the strip rest on the platforms with each support platform supporting two adjacent corners of the strip. Each support platform includes a step which engages the ends of the strip. The support platforms are magnetized to hold the strip in place. Accordingly, since all four of the corners of the strip are supported on a pair of magnetized support platforms, the strip is held in place during measurement. Two posts extend from the fixture to engage one side of the strip in order to locate it relative to the support platforms. The indicating gage includes a plunger extending through the fixture to engage the longitudinally curved surface at substantially its midpoint, thereby providing an easy measurement of the deflection (arc height) of the test. The platforms are magnetized by magnets which are adjustable relative to the platforms to allow the operator to control the magnitude of the force holding the test strip in place. Because the strips are so small, too great of a force makes it difficult for the operator to easily remove the strip. The shoulders on the platform and the posts permit the operator to easily locate the strip relative to the gage tip when the strip is placed on the fixture.

DETAILED DESCRIPTION OF INVENTION

Figure 1:
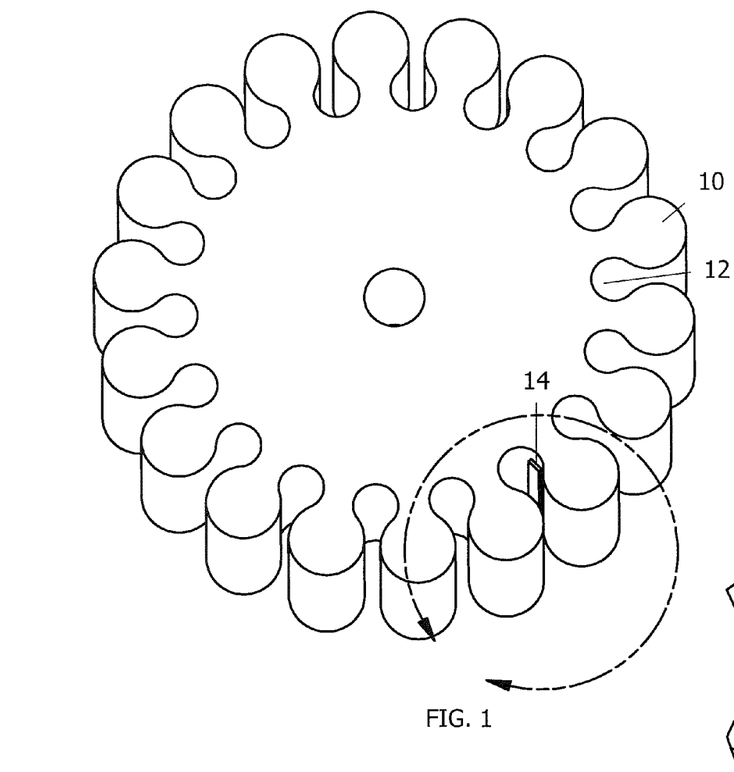
FIG. 1 is a view in perspective of a product which undergoes peening and which has recesses and crevices which are subject to peening.
Figure 2:
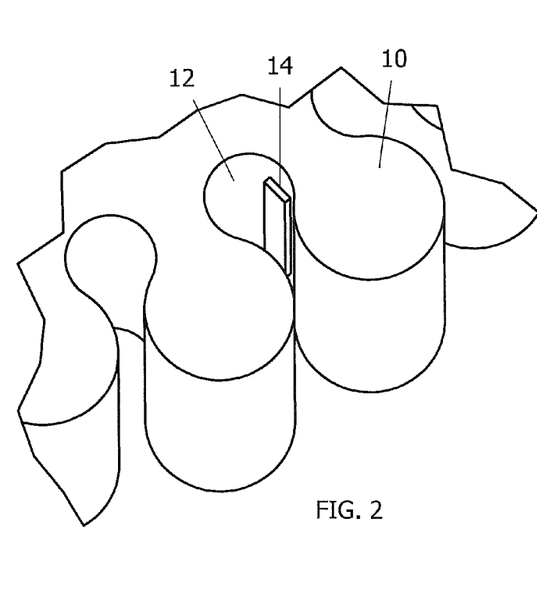
FIG. 2 is a large view of the circumscribed portion of FIG. 1.
Figure 3:
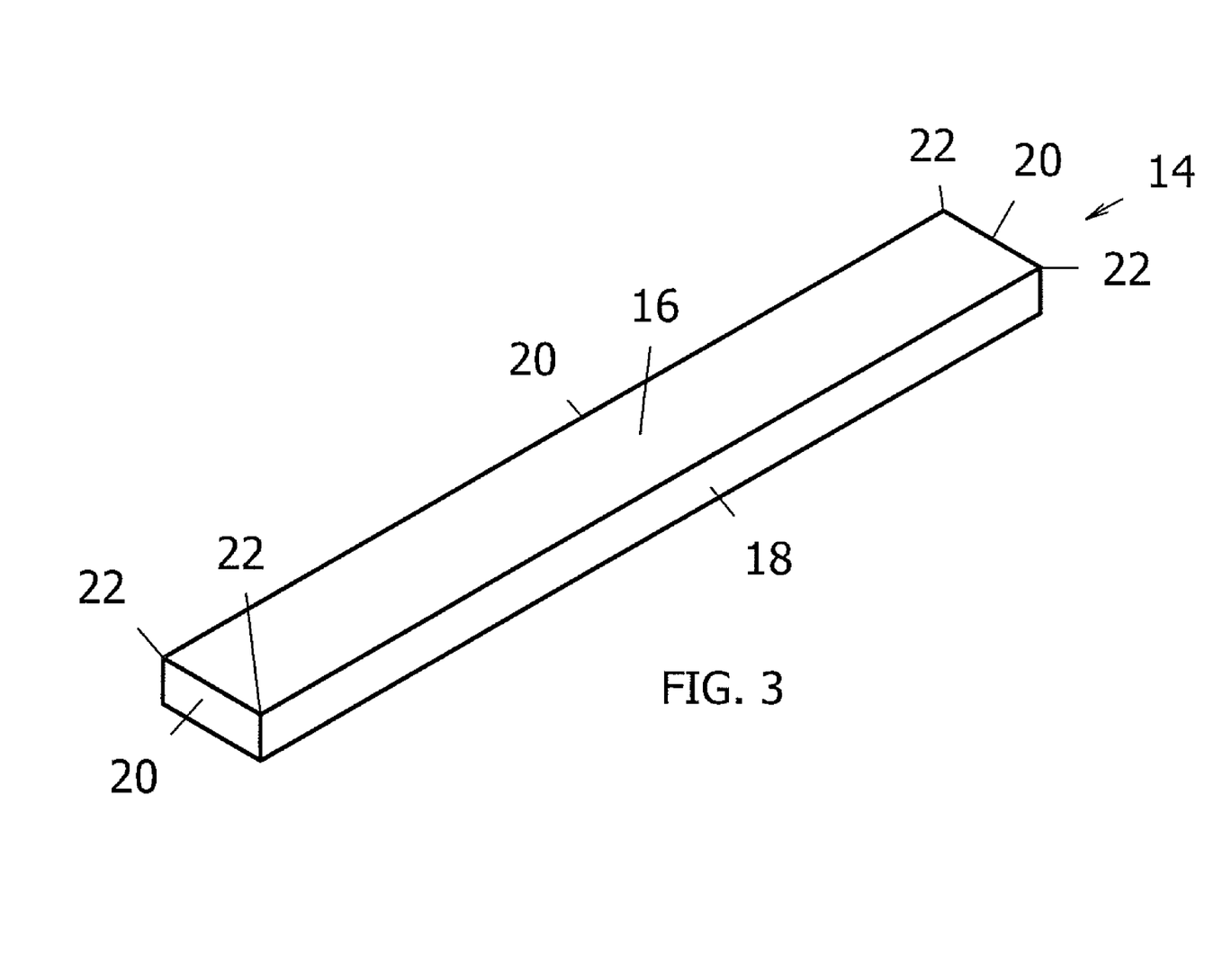
FIG. 3 is a view in perspective of a mini-strip that is peened to determine the intensity of shot peening according to the present invention.

Referring now to FIGS. 1-3, FIG. 1 illustrates a typical complex part which is treated by peening. The part is indicated by reference numeral 10, and includes multiple crevices 12 which cannot be easily peened directly, so that peening is dependent upon the shot peening media ricocheting into the crevices. Accordingly, the intensity of the peening within the crevices 12 cannot be easily established with conventional Almen strips. Accordingly, since a conventional Almen strip (measuring three inches by three quarters of an inch) is too large to fit into the cavities 12, a mini-strip, as illustrated at 14 and FIG. 3, is secured in one of the crevices 12 (FIG. 2) by a releasable adhesive, e.g. rubber cement. A mini-strip 14 includes an upper surface 16 which is exposed to peening and a lower surface 16A on which the deflection (arc height) is measured, opposite longitudinally extending side surfaces 18, and transverse end surfaces 20. The upper surface 16, lower surface 16A longitudinal surfaces 18 and end surfaces 20 meet at corners 22.

Figure 4:
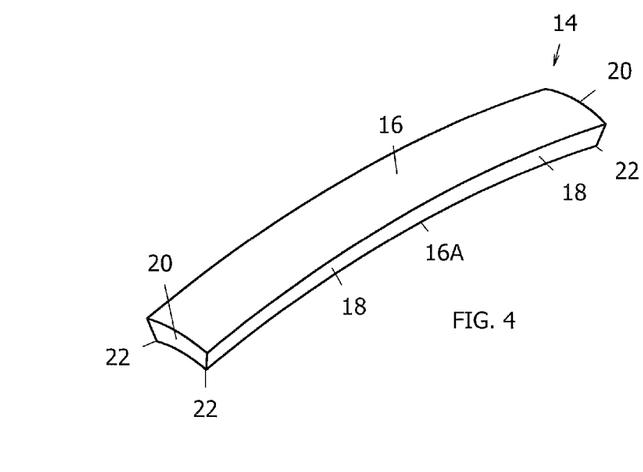
FIG. 4 is a view similar to FIG. 3, but of a mini-strip that has undergone peening.
Figure 7:
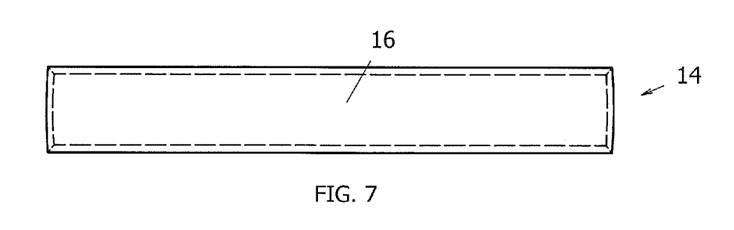

Referring to FIGS. 4, 7, after peening, the test strip 14 will become curved in both the longitudinal and transverse directions. In FIGS. 4, 7, the test strip 14 is placed into position for measurement with the peened surface 16 upward and the un-peened surface 16A being contacted by the gage plunger 28. To determine the intensity of the peening that has taken place, the deflection (arc height) of the strip 14 must be measured. That deflection (arc height) is the vertical distance from the coplanar surface of the lower portion 44 of the platforms 36, 38, 64, 66 to the lower surface 16A of the strip. Since the strip 14 is only one eighth of an inch wide, prior art Almen gages cannot be used.

Figure 5:
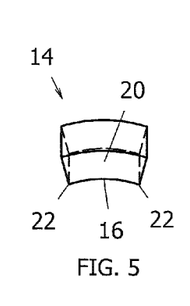
FIGS. 5, 6 and 7 are end views, a side view and a top view of mini-strip illustrated in FIG. 4.
Figure 6:
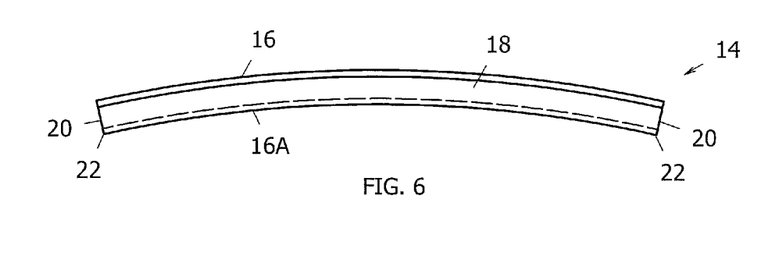
Figure 8:
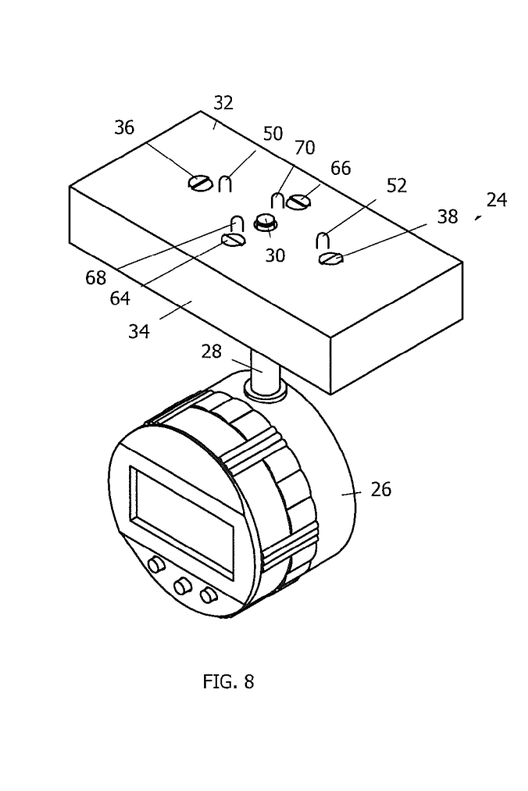
FIG. 8 is a view in perspective of a measuring gage made pursuant to the present invention used to measure the deflection (arc height) of the mini-strip illustrated in FIGS. 4-7.
Figure 9:
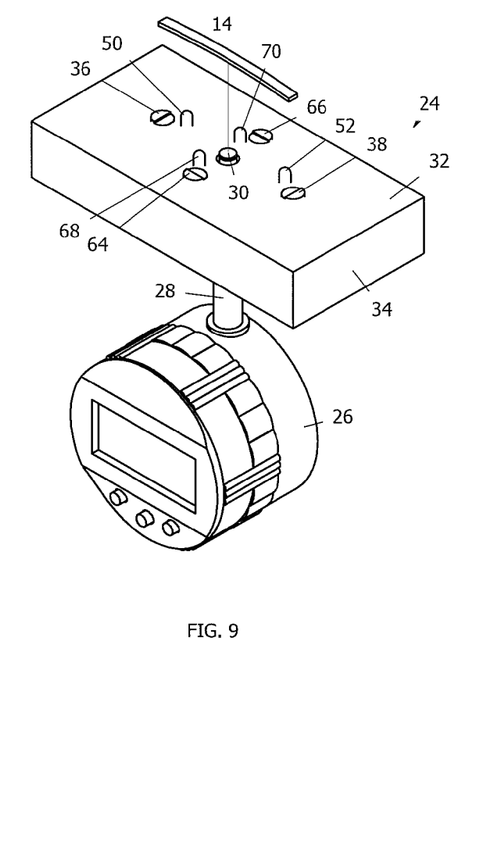
FIG. 9 is similar to FIG. 8, but illustrating placement of a two inch mini-strip on the fixture.
Figure 10:
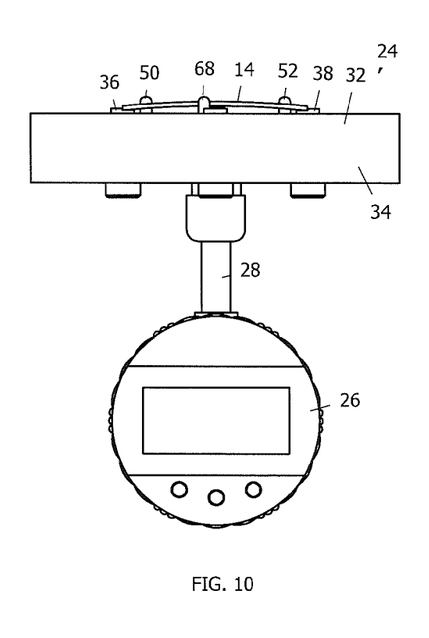
FIG. 10 is a side view of the fixture illustrated in FIGS. 8 and 9 illustrating the two inch mini-strip in position for measuring.
Figure 11:
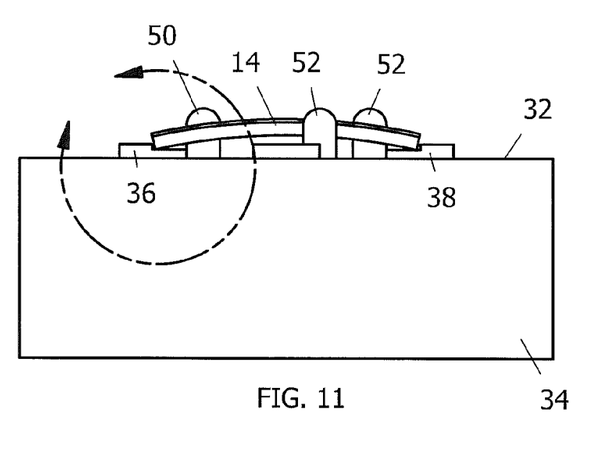
FIG. 11 is an enlarged view of the support platform illustrating a mini-strip installed thereon.
Figure 12:
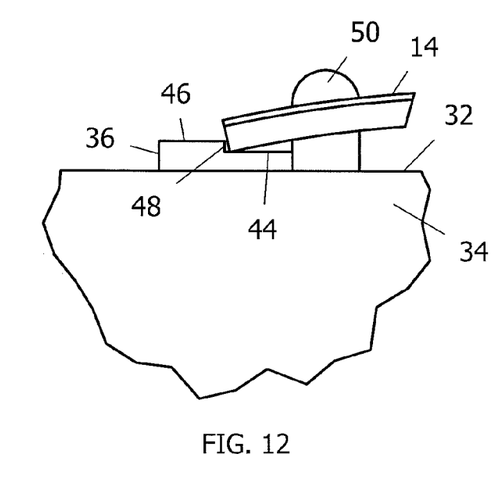
FIG. 12 is an enlarged fragmentary view of the circumscribed portion of FIG. 11.

As illustrated in FIGS. 4-6, after peening, the corners 22 are all separated by curved surfaces, therefore, the corners 22, if they rest on a common plane, will support the strip 14 in a stable position, permitting the deflection to be measured. Accordingly, and referring to FIGS. 8-10, the strip 14 is measured on a gage generally indicated by the numeral 24. The gage 24 includes a digital indicator 26 which is responsive to the displacement of a plunger 28 which extends through a central opening 30 in the substantially flat upper surface 32 of a fixture 34. Conventionally, the indicator 26 and fixture 34 can be mounted on a support stand of the same general type illustrated in U.S. Pat. No. 5,297,418. The fixture 34 is made from a non-magnetic material, such as aluminum. A pair of substantially circular support platforms 36, 38 are mounted within bores 40, 42 (FIG. 13) in the fixture 34. Bores 40 and 42 are collinear with the bore 30 through which the plunger 28 extends. Each of the platforms 40, 42 has a diameter marginally larger than the width of the mini-strip 14, and is stepped to define a lowered portion 44 and a raised portion 46 with a shoulder 48. The shoulder 48 of each of the platform 36, 38 is separated by a distance marginally larger than the length of the mini-strip 14. A pair of posts 50, 52 are mounted adjacent each of the platforms 36, 38, and are offset by a distance equal to approximately one half of the width of the mini-strip 14. Accordingly, the posts 48, 50 and the shoulders 48 assist the user in placing the mini-strip in its proper position on the fixture 34 for the measurement.

Figure 13:
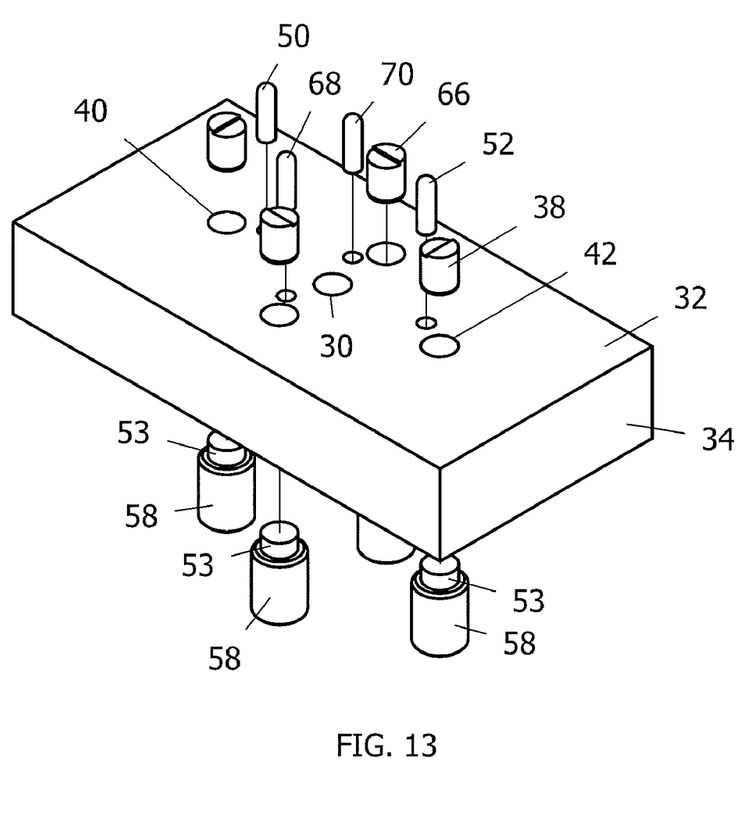
FIG. 13 is an exploded view of the support fixture illustrating the support platforms and their associated magnets, as well as the locating posts.
Figure 14:
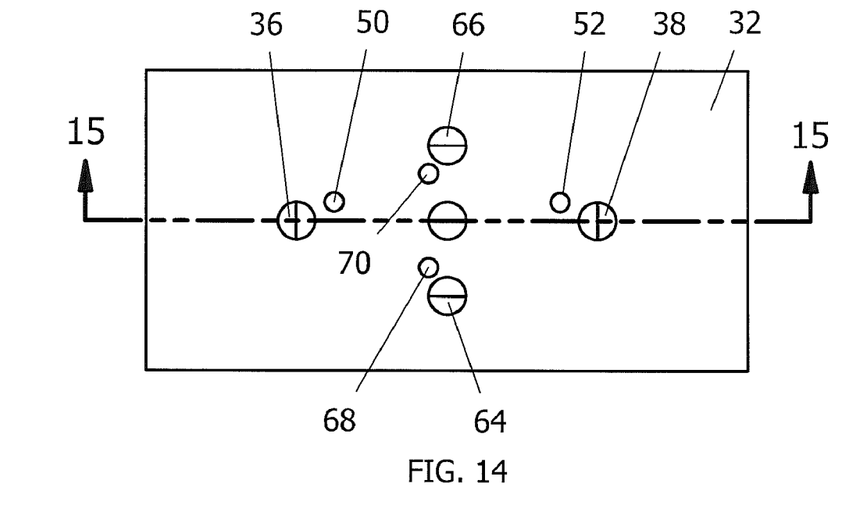
FIG. 14 is a top plan view of the fixture with the platforms and posts installed.
Figure 15:
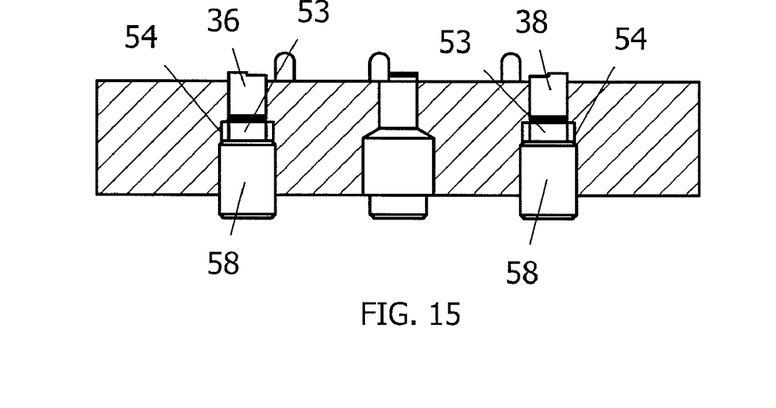
FIG. 15 is a cross sectional view taken substantially along lines 15-15 of FIG. 14.
Figure 16:
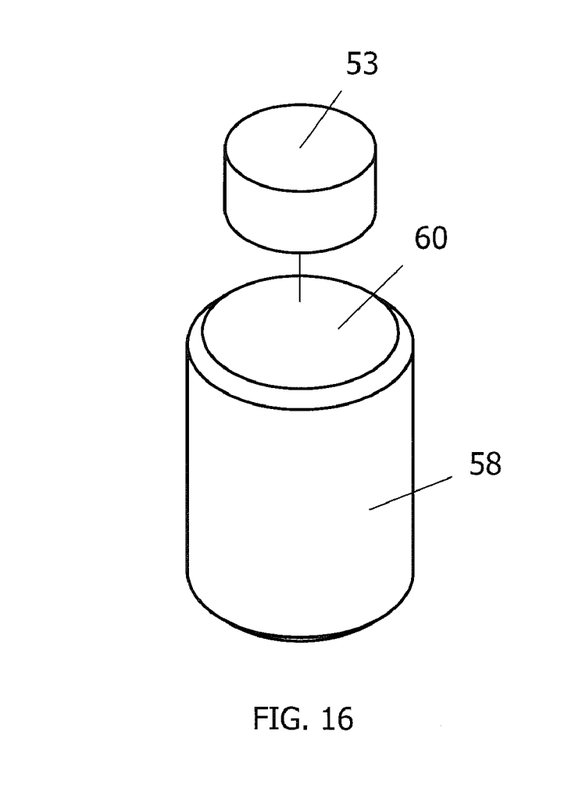
FIG. 16 is an exploded view of the magnets used in FIGS. 13-15.

The mini-strips 14 are made of a magnetic material as are the platforms 36, 38. Magnets 53 are mounted in the bores 40, 42 just below the platforms 36, 38, as illustrated in FIGS. 13 and 15. The magnets 53 are movable within the bores 40, 42 toward and away from the platforms 36, 38. Bores 40 and 42 further include larger diameter portions 54, 56, which may be threaded to receive an adjustment mechanism 58. Magnets 53 are secured to the upper surface 60 of adjustment mechanism 58, which may be threaded to engage corresponding threads on larger portions 54, 56 of bores 40, 42. Accordingly, magnets 53 may be advanced or retracted within the bores 40, 42, to thereby vary the magnetic attraction of the platforms 36, 38.

As discussed above, since the strips 14 are so narrow, they are difficult to place and remove on the measuring platform 34. Accordingly, the posts 50, 52 and shoulders 48 are provided to guide the operator in placement of the strips 14, however, the magnetic attraction of platforms 36, 38 holding the strips in place cannot be too small or the strip is easily displaced by the gage plunger, resulting in corrupted measurements. If the force is too large, removal of the strip is very difficult. Accordingly, by adjusting the position of the magnets 53, the magnetic force holding the mini-strip 14 in position may be varied so that the force is optimum.

As illustrated in the FIGS. 8, 9, 10, 11, 13, and 15, a second set of platforms 64, 66 are mounted in corresponding bores in the fixture 34, and are used to read the shorter mini-strip. Platforms 64, 66 are also provided with magnets and adjustment magnet mechanisms identical to the magnets 53 and adjustment mechanisms 58. A second set of posts 68, 70 are provided to enable the displacement of the shorter mini-strip to be measured using the same fixture and indicator as is used to measure the longer strip 14.

The invention is not limited to the details given above, but may be modified within the scope of the following claims.

What is claimed is:

1. Method for determining shot peening or blasting intensity including the steps of peening or blasting a test strip defined by corners defining the longitudinal and transverse dimension of said test strip, said test strip after treatment being defined by longitudinally and transversely curved surfaces extending between said corners, placing the test strip on a fixture having a flat surface substantially common to each of said four corners and supporting a pair of support platforms, each of said support platforms including a support portion extending between a corresponding pair of said corners defining said transverse dimension of said test strip, and measuring the deflection of one of said curved surfaces relative to said flat surface.

2. Method as claimed in claim 1, wherein said platforms are magnetized, and the test strip is retained on said platform by the magnetic attraction of said platforms.

3. Method as claimed in claim 2, wherein said platforms are magnetized by magnets mounted in said fixture below each of said platforms.

4. Method as claimed in claim 2, wherein each of said platforms are stepped to define a raised portion and a shoulder between said raised portion and said flush portion, and restraining longitudinal movement of said strip by said shoulders.

5. Method as claimed in claim 3, wherein said magnets are moved toward and away from their corresponding platforms to control the magnitude of the magnetic attraction of the platforms.

6. Method as claimed in claim 1, wherein each of said platforms are stepped to define a shoulder, and restraining longitudinal movement of said strip by said shoulders.

7. Method as claimed in claim 1, wherein the deflection of said longitudinally curved surface is measured.

8. Gage for measuring the displacement of said test strip used to measure the intensity of shot peening treatment defined by corners defining the longitudinal and transverse dimension of said test strip, comprising a fixture having a substantially flat support surface, a pair of support platforms carried by said support surface and spaced on said support surface a distance substantially equal to the length of said test strip, each of said platforms having a flat portion supporting the test strip on the flat surface, each said platform being wide enough to support adjacent transversely separated corners of said test strip after the test strip has been treated sufficiently to establish longitudinally and transversely curved surfaces, and an indicator measuring the displacement of said longitudinally curved surface from said flat support surface when the adjacent transversely separated corners of the test strip are supported on their corresponding platforms.

9. Gage as claimed in claim 8, wherein a distance measuring indicator includes a plunger extending through said fixture to engage said longitudinally curved surface to measure the displacement of the latter relative to said support surface.

10. Gage as claimed in claim 9, wherein a second pair of platforms are offset transversely at said plunger from said first pair of platforms.

11. Gage as claimed in claim 9, wherein each of said platforms are stepped to define a shoulder and restraining longitudinal movement of said strip by said shoulders.

12. Gage as claimed in claim 8, said platforms are magnetized, and said test strip is retained on said platforms by the magnetic attraction of said platforms.

13. Gage as claimed in claim 12, wherein said platforms are magnetized by magnets mounted in said fixture below each of said platforms.

14. Gage as claimed in claim 13, wherein said magnets are movable relative to said platforms, and an adjustment mechanism controls the distance between the magnets and the platforms to thereby vary the magnetic attraction of the platforms.

\* \* \* \* \*